(12) United States Patent
Battenberg et al.

(10) Patent No.: US 7,010,445 B2
(45) Date of Patent: Mar. 7, 2006

(54) AUTOMATED FAULT DIAGNOSIS DEVICE AND METHOD

(75) Inventors: Rexford A. Battenberg, Knoxville, TN (US); J. Brent Van Voorhis, Kingston, TN (US); James C. Robinson, Knoxville, TN (US); Jason E. Hillard, Knoxville, TN (US)

(73) Assignee: CSI Technology, Inc., Wilmington, DE (US)

( * ) Notice: Subject to any disclaimer, the term of this patent is extended or adjusted under 35 U.S.C. 154(b) by 0 days.

(21) Appl. No.: 10/460,967

(22) Filed: Jun. 13, 2003

(65) Prior Publication Data

US 2003/0209077 A1    Nov. 13, 2003

Related U.S. Application Data

(63) Continuation-in-part of application No. 10/055,473, filed on Jan. 23, 2002, now Pat. No. 6,618,128.

(51) Int. Cl.
*G06F 3/05*  (2006.01)

(52) U.S. Cl. .............................. 702/77; 702/59; 702/60; 702/76

(58) Field of Classification Search ................. 702/39, 702/54, 71, 75, 76, 180–183, 66, 59, 60, 702/189, 190; 235/454; 370/319; 717/138
See application file for complete search history.

(56) References Cited

U.S. PATENT DOCUMENTS

| | | | |
|---|---|---|---|
| 3,654,553 A | 4/1972 | Mary et al. | 324/175 |
| 3,687,517 A | 8/1972 | Brun | 356/28 |
| 3,689,157 A | 9/1972 | Andermo | 356/28 |
| 3,804,517 A | 4/1974 | Meyr et al. | 356/28 |
| 3,804,518 A | 4/1974 | Meyr | 356/28 |
| 3,824,015 A | 7/1974 | Petit et al. | 356/28 |
| 3,885,873 A | 5/1975 | Andermo | 356/28 |
| 4,031,466 A | 6/1977 | Krause et al. | 324/175 |
| 4,167,330 A | 9/1979 | Haville | 356/28 |
| 4,181,432 A | 1/1980 | Flower | 356/28 |
| 4,204,115 A | 5/1980 | Boldridge, Jr. | 250/227 |
| 4,312,592 A | 1/1982 | Sabater et al. | 356/28 |
| 4,329,047 A | 5/1982 | Kikuchi et al. | 356/28 |
| 4,387,785 A | 6/1983 | Fromm | 181/142 |

(Continued)

FOREIGN PATENT DOCUMENTS

DE    199 07454    8/2000

(Continued)

*Primary Examiner*—Marc S. Hoff
*Assistant Examiner*—Felix Suarez
(74) *Attorney, Agent, or Firm*—Luedeka, Neely & Graham, P.C.

(57) ABSTRACT

A diagnostic apparatus and method for sensing a signal emanating from a machine and determining a periodic machine event based on the emanated signal. The apparatus includes analog to digital processing components for digitizing the sensed signal, producing a digitized signal. The apparatus also includes a transform algorithm, memory, an analysis algorithm, and a display. The transform algorithm transforms the digitized signal to generate power spectral density and autocorrelation data which is stored in the memory. The analysis algorithm includes criteria for analyzing the stored power spectral density and autocorrelation data to determine a period machine event based at least in part upon the autocorrelation data. The display displays the periodic machine event to a user. In the event of a suspected defect or fault, the device alerts the user. The user may then elect to proceed with repairs or undertake advanced analysis of the suspected fault as economy dictates.

23 Claims, 5 Drawing Sheets

U.S. PATENT DOCUMENTS

| | | | | |
|---|---|---|---|---|
| 4,551,018 | A | 11/1985 | Mannava et al. | 356/285 |
| 4,601,580 | A | 7/1986 | Halliwell | 356/349 |
| 4,638,155 | A | 1/1987 | Dorr | 250/231 |
| 4,774,463 | A | 9/1988 | Mizobuchi et al. | 324/175 |
| 4,866,268 | A | 9/1989 | Tang et al. | 250/231 |
| 4,880,966 | A | 11/1989 | Goodrich et al. | 250/231 |
| 4,968,145 | A | 11/1990 | Takiguchi | 356/354 |
| 5,059,901 | A | 10/1991 | Van Voorhis | 324/175 |
| 5,214,278 | A | 5/1993 | Banda | 250/231.14 |
| 5,251,151 | A | 10/1993 | Demjanenko et al. | 364/550 |
| 5,365,787 | A | 11/1994 | Hernandez et al. | 73/660 |
| 5,394,473 | A * | 2/1995 | Davidson | 704/200.1 |
| 5,424,824 | A | 6/1995 | Daiber et al. | 356/285 |
| 5,445,028 | A | 8/1995 | Bianchi et al. | 73/593 |
| 5,501,226 | A | 3/1996 | Petersen et al. | 128/691 |
| 5,526,109 | A | 6/1996 | Johnson | 356/285 |
| 5,541,732 | A | 7/1996 | Forin | 356/373 |
| 5,610,339 | A | 3/1997 | Haseley et al. | 73/660 |
| 5,612,544 | A | 3/1997 | Busch | 250/556 |
| 5,636,014 | A | 6/1997 | Hanson | 356/28 |
| 5,646,340 | A | 7/1997 | Gee et al. | 73/116 |
| 5,701,172 | A | 12/1997 | Azzazy | 356/28 |
| 5,872,628 | A | 2/1999 | Erskine | 356/345 |
| 5,974,380 | A * | 10/1999 | Smyth et al. | 704/229 |
| 6,208,944 | B1 | 3/2001 | Franke et al. | 702/56 |
| 6,215,408 | B1 * | 4/2001 | Leonard et al. | 340/644 |
| 6,233,045 | B1 | 5/2001 | Suni et al. | 356/28.5 |
| 6,289,735 | B1 | 9/2001 | Dister et al. | 73/579 |
| 6,542,739 | B1 * | 4/2003 | Garner | 455/427 |
| 2001/0055320 | A1 * | 12/2001 | Pierzga et al. | 370/480 |

FOREIGN PATENT DOCUMENTS

| | | |
|---|---|---|
| JP | 2022521 | 1/1990 |

* cited by examiner

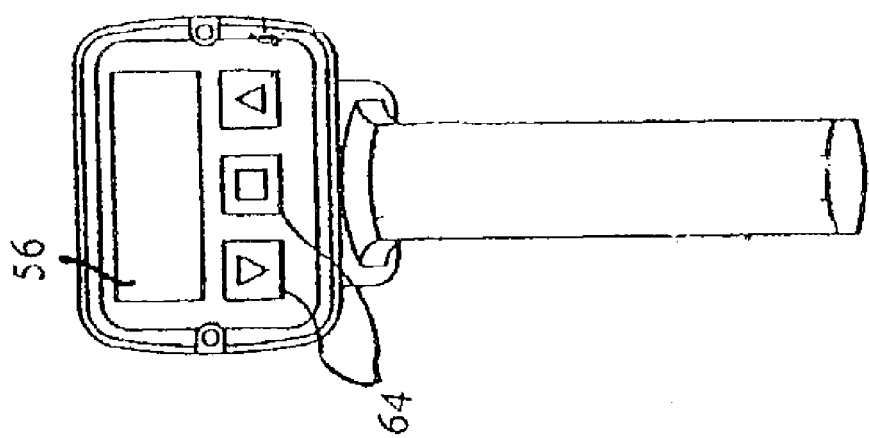

AUTOMATED FAULT DIAGNOSIS DEVICE AND METHOD

RELATED APPLICATIONS

This application for letters patent is a continuation-in-part of application Ser. No. 10/055,473 to Van Voorhis et al. filed on Jan. 23, 2002, now U.S. Pat. No. 6,618,128.

FIELD OF THE INVENTION

This invention relates generally to fault diagnostic systems and methods. More particularly, this invention relates to an automated fault diagnostic device and method for determining operational states of a machine or other system by detecting and analyzing vibrations and sound waves utilizing ultrasonic and sonic characterization information.

BACKGROUND

The normal frequency range for human hearing (sonic range) is roughly 20 to 20,000 hertz. Ultrasonic sound waves have frequencies above the frequency range of human hearing. Accordingly, any frequency above 20,000 hertz may be considered ultrasonic. Most industrial processes, including almost all sources of friction, create some ultrasonic noise. For example, leaks in pipes, machinery defects, and electrical arcing produce sonic or audible sound waves, as well as, ultrasonic sound waves.

In the past, handheld diagnostic instruments, such as ultrasonic "guns", have utilized both sonic and ultrasonic sensors for monitoring machinery health. These older instruments provide a quick check of a machine's condition and do not typically perform extensive analysis. Often, these instruments allow a user to audibly listen to the machinery sound or vibration, and provide a method of measuring the magnitude of the sound or vibration. Heterodyning inaudible signals (i.e. ultrasonic signals) provides an audible representation of the signals in the sonic range, enabling a user to hear the signals.

An analog meter, bargraph, or digital display are used to indicate the vibration amplitude or magnitude. Some instruments may include peak, peak hold, averaging, and other signal conditioning functions to increase the possibility of a successful diagnosis. Other instruments output the vibration signal to an external instrument, such as an oscilloscope, data collector, or a Fourier Transform analyzer. Such practice, while sometimes necessary to make a likely diagnosis, is time consuming and requires a user to have some level of analysis skill.

Most of these prior art instruments rely heavily upon the observation, skill, and experience of the user to provide a diagnosis of a machine's health. Additionally, machinery faults can remain undetected when a fault is masked by background noise or when signals unrelated to the defect are present.

It has been found that certain machine faults reveal themselves in unique frequency ranges. Leak detection, for example, generally works well at an ultrasonic frequency of around 40 kHz. In rotating machinery, lubrication problems can be reliably detected at approximately 30 kHz. Mechanical bearing defects, especially those in the larger bearings found in industrial environments, are best detected in a frequency band of about 2–6 kHz. Some instruments provide quantitative measurements in selected frequency bands. This allows a skilled user to better diagnose and identify the type of fault that is occurring. However, the user of the instrument must still rely primarily on his skill level and judgment to identify the fault.

What is needed, therefore, is a device and a method which provides automated fault diagnosis of a system which overcomes the shortcomings associated with prior art instruments.

SUMMARY

In accordance with one embodiment, a method is disclosed for determining a periodic event of a machine system. The method provides for receiving signals emanating from the system; transforming the received signals to produce first transformed signals; transforming the first transformed signals to produce second transformed signals having at least real components, and processing the transformed signals using select criteria to determine the periodic system event.

In accordance with an embodiment, a sound sensing device is operable to sense sound and determines a periodic event of a machine based thereon. Sound signals are defined to include sonic, subsonic, and ultrasonic sound signals and variants thereof. The device includes a sensor for sensing a sound signal emanating from the machine and converting the sensed sound signal into an electrical signal. Signal processing components digitize the electrical signal and process the digitized signal. The device also includes firmware. The firmware includes transform algorithms for successively transforming the digitized signal to produce first and second sets of transform data, the second set being a transform of the first set. Analysis algorithms analyze the two sets of transform data to determine a periodic machine event based on select criteria applied to the transform data.

In yet another embodiment, a diagnostic apparatus is operable to sense a signal emanating from a machine and determine a periodic machine event based on the emanated signal. The apparatus includes analog to digital processing components for digitizing the sensed signal, producing a digitized signal. The apparatus also includes a transform algorithm, memory, an analysis algorithm, and a display. The transform algorithm transforms the digitized signal to generate power spectral density and autocorrelation data which is stored in the memory. The analysis algorithm includes criteria for analyzing the stored power spectral density and autocorrelation data to determine a period machine event based at least in part upon the autocorrelation data. The display displays the periodic machine event to a user.

BRIEF DESCRIPTION OF THE DRAWINGS

Further advantages of the invention will become apparent by reference to the detailed description of preferred embodiments when considered in conjunction with the figures, which are not to scale, wherein like reference numbers, indicate like elements through the several views, and wherein.

FIG. 3 is a rear-end view of an automated diagnostic device of FIG. 1; and,

DETAILED DESCRIPTION

Figure 1:
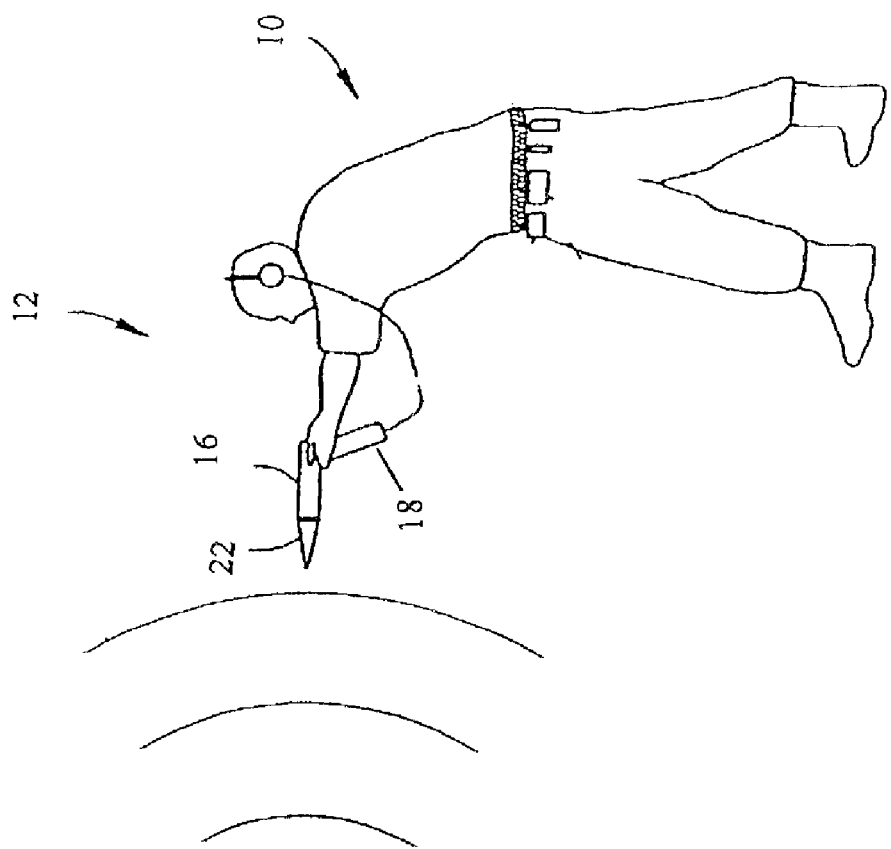
FIG. 1 depicts a user pointing an automated diagnostic device at a system.

Referring to the Figures, FIG. 1 depicts a user 10 pointing a diagnostic device 12 at a system 14. As described below, when activated by user 10 to diagnose a system's operational state, the device 12 automatically provides a system diagnostic or state to the user 10. The system 14 generally includes various electrical and mechanical components which control the system's operation. It will be understood that the invention is not intended to be limited to contact type sensing and is applicable to airborne signal sensing applications and the like as well.

After a period of time and use, the system's components may develop faults or other undesirable operational characteristics. Thus, periodically, the system 14 must be inspected to determine its current operational state and whether the system 14 is functioning above a predetermined operational standard. For example, if a motor is not operating at an optimal efficiency, it becomes necessary to determine what may be causing the inefficiency.

It is inefficient and inconvenient to disassemble a system into individual component parts and to thereafter inspect each part for failures or faults. Thus, it is preferable to diagnose a system's health without having to go through the time-consuming disassembly of the system 14 into individual component parts. The device 12 automatically provides an operational characteristic of a system 14 without having to disassemble the system into its component parts.

U.S. Pat. Nos. 6,220,098, 6,234,021, and 6,247,353 disclose an ultrasonic device which receives and conditions ultrasonic and sonic waveforms, and are hereby incorporated by reference. Audible signal representations enable a user to determine if there are faults present in a system. The device 12 disclosed herein improves the operational diagnostics provided by these devices, and enables a user 10 to automatically diagnose the health or state of a machine or other system 14, as described below.

According to one aspect, the present device 12 provides a solution and/or other information to a user 10 of the device 12, secondary computer, or other diagnostic/analyzing system. Wireless and traditional signal conveyance methods can be used to transfer the solution and other information from the device 12 to a desired location.

Referring again to FIG. 1, a user 10 operates a diagnostic device 12, according to a preferred embodiment of the invention. The device 12 is preferably both automated and portable, and it measures sonic and ultrasonic sound and temperature. In addition, the device 12 performs an analysis of sound and temperature information. The device 12 measures surface temperatures while also detecting sonic and ultrasonic sounds produced by sources such as leaks in pipes, arcing, electrical corona, machinery defects and the like. The device 12 can automatically analyze the measurements and detections to determine operational information of the system 14 being diagnosed.

Figure 2:
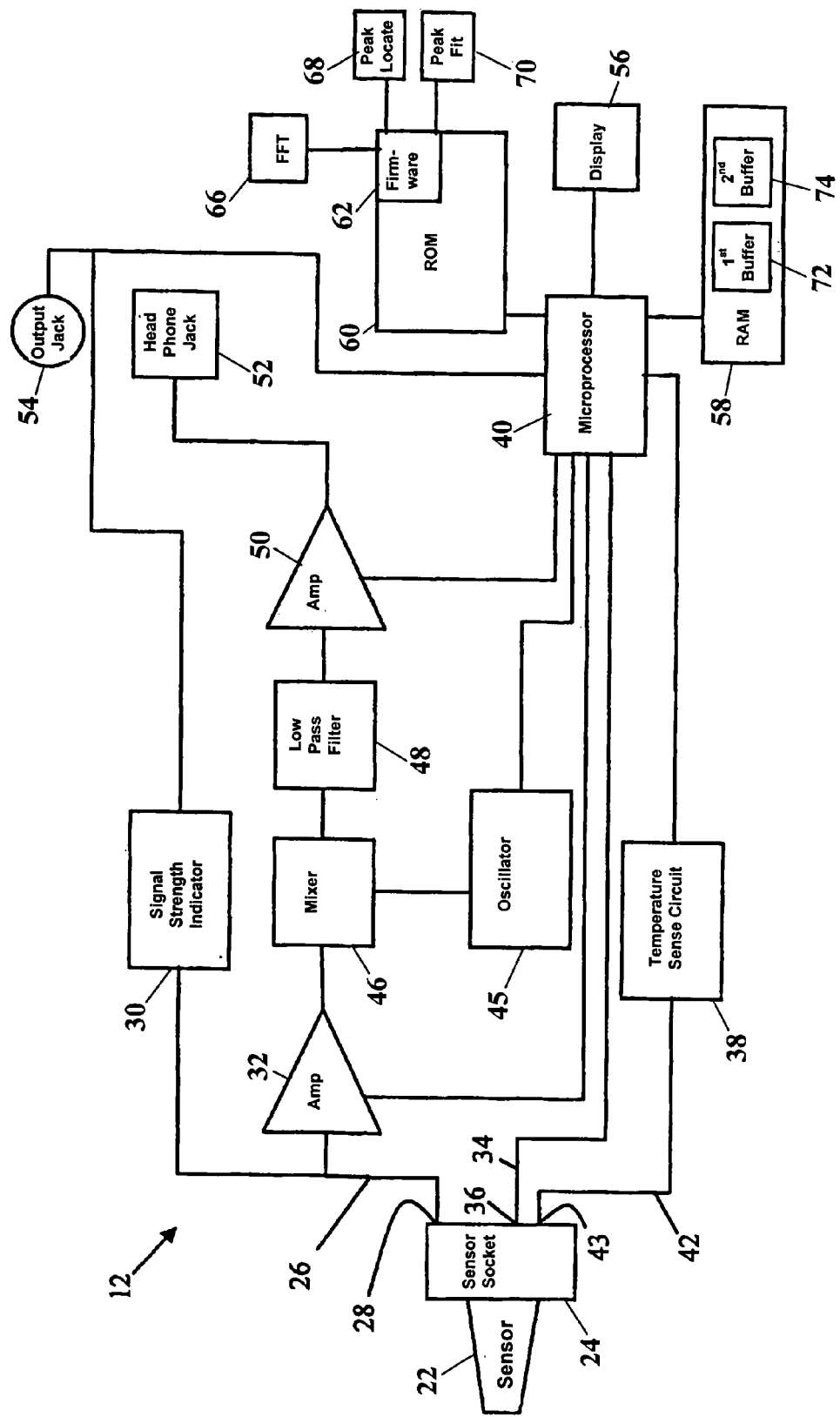
FIG. 2 is a schematic diagram depicting various electrical components of an automated diagnostic device.

As described in the above incorporated-by-reference patents, the device 12 includes an elongate housing 16 having a grip 18. The grip 18 provides a handle enabling a user 10 to carry and point the device 12 at a system 14, as depicted in FIG. 1. The device 12 also includes a trigger which, when actuated, controls the device's operation. The device 12 further includes a type of sensor 22 and a sensor socket 24 (FIG. 2). Multiple sensors 22 are available which can be removably installed in the sensor socket 24. Each sensor 22 preferably contains encoded identification information enabling the device 12 to recognize the type of sensor 22 installed in the socket 24 and configure its operation to the installed sensor 22. A user 10 can select which sensor 22 to install in the sensor socket 24 depending upon a particular diagnostic application.

Referring now to FIG. 2, the device 12 includes various electrical features, including a number of signal processing components. Electrical output line 26 electrically connects the socket output 28 with received signal strength indicator 30 and a voltage controlled amplifier 32. Electrical output line 34 electrically connects the socket output 36 with a temperature sense circuit 38 which is electrically connected to a microprocessor 40. The microprocessor 40 controls various aspects of the device 12, as described below. Electrical output line 42 electrically connects the socket output 43 with the microprocessor 40. The sensor socket 24 outputs the received signals to the various signal processing components.

The device 12 also includes a variable frequency sine wave oscillator 45 electrically connected to the microprocessor 40 and a mixer 46. The microprocessor 40 controls the variable frequency sine wave oscillator 45 which provides oscillation signals to the mixer 46 based on the sensed signal frequencies and/or user inputs to the device 12. The mixer 46 output is electrically connected to a low-pass filter 48 which filters signals having frequencies above a predetermined range.

While it is preferred to use discreet analog devices, such as amplifier 37, mixer 46, oscillator 45, filter 48, and voltage controlled amplifier 50, these devices may be combined into a single device such as an ASIC or one or more digital devices, such as a microprocessor system. References to filters, oscillators and other discrete devices also refer to digital implementations of those devices.

The low-pass filter 48 output is electrically connected to a second voltage controlled amplifier 50. The second voltage controlled amplifier is electrically connected to a headphone jack 52 and the microprocessor 40. Headphones can be connected to the headphone jack 52 which receives the audible frequency range signals from the low-pass filter 48, broadcasting the audible frequency range signals to the user 10 of the device 12. The audible signals provide further information to the user 10 in determining the operational state of the system 14.

The microprocessor 40 is also electrically connected to an output jack 54 for outputting signals to another device. A display 56 is also electrically connected to the microprocessor 40 and operates to provide a visual display to the user 10. Random access memory (RAM) 58 and read-only memory (ROM) 60 also electrically connect to the microprocessor 40. Preferably, ROM 60 includes firmware 62 which includes various algorithms for enhancing the diagnostic capability of the device 12. The firmware 62 includes signal processing capabilities for analyzing and determining operational information about the system 14 from signals received by the device 12.

The device 12 includes keypads 64 (FIG. 3) readily accessible to the user 10. Various parameters, such as signal amplitude, surface temperature, peak frequency, harmonics, etc. may be displayed to the user 10 by manipulating the keypads 64. The keypads 64 allow a user 10 access to several menus and options, as well as providing user control over such functions as headphone volume and heterodyne frequency selection.

The voltage controlled amplifier 32 amplifies the signals received by device 12. The microprocessor 40 controls the oscillator 45 to output local oscillator frequency signals to the mixer 46. The mixer 46 receives the electrical signals from the amplifier 32 and the local oscillator frequency signals from the variable frequency sine wave oscillator 45. When the received signals are ultrasonic, the mixer 46 heterodynes the local oscillator frequency and amplified electrical signals to produce audible frequency range signals. The audible frequency range signals correspond to the ultrasonic electrical signals but are in the audible frequency range of a human being.

The low-pass filter 48 receives the audible frequency range signals from the mixer 46. The low-pass filter 48 is preferably tuned to remove any signals having frequencies above the audible frequency range. After the signals pass through the low-pass filter 48, voltage controlled amplifier 50 amplifies the signals output from the low-pass filter 48. As described below, the microprocessor 40 and firmware 62 analyze the signals preferably utilizing an autocorrelation method, including additional processing enhancements which enables the device 12 to detect and process periodic signals that are indicative of an operational state of the system 14, such as a machinery fault.

The device 12 performs measurements in several frequency bands, and each frequency band is preferably biased toward a particular machine fault. As an example, detection of periodic vibration in a machine can be indicative of a fault in a rotating element, such as a bearing. Various operational states of the machine would include unhealthy or malfunctioning, semi-healthy, and healthy states. Knowledge of the various machine states allow a user 10 to determine the machine's efficiency and whether the machine requires maintenance or replacement of an inefficient or faulty machine component.

The signals presented to the microprocessor 40 are analog electrical time domain signals, having complex signal patterns. The microprocessor 40 includes analog-to-digital (A/D) signal processing components for digitizing the electrical time domain signals. The device 12 also includes Fourier Transform algorithms for transforming the digitized signals into the frequency domain or a frequency spectrum. The Fourier Transform algorithms operate upon the time domain signals, utilizing a Fourier Transform function 66 included in the firmware 62 of the device 12 (FIG. 2). It will be appreciated that the Fourier Transform function 66 may include other processing capabilities, including discrete Fourier and fast Fourier processing.

After the digital signal processing components digitize the analog signals, the Fourier Transform function 66 converts the digital time domain signals to the frequency domain, creating power spectral density data or frequency spectra. The power spectral density data corresponds to the received signals emanating from the system 14. The device 12 can determine the operational state(s) of the system 14 by performing various mathematical operations on the power spectral density data.

With continuing reference to FIG. 2, the firmware 62 includes a peak location algorithm 68 and peak fit algorithm 70. The firmware 62 also includes instructions for storing signals into a number of frequency bins. Due to a finite number of frequency bins, the algorithms enhance the frequency measurement accuracy by interpolation between the frequency bins. The peak location algorithm 68 can locate the fundamental peak of a lowest order major harmonic family. The peak fit algorithm 70 can "fit" a curve to the frequency spectra, including the higher amplitude peaks in a harmonic family. The peak fit algorithm 70 increases the precision of the frequency measurement by interpolating between the finite number of frequency bins, enhancing the location of a peak which improves the device's ability to determine an operational state of a system 14.

Figure 4A:
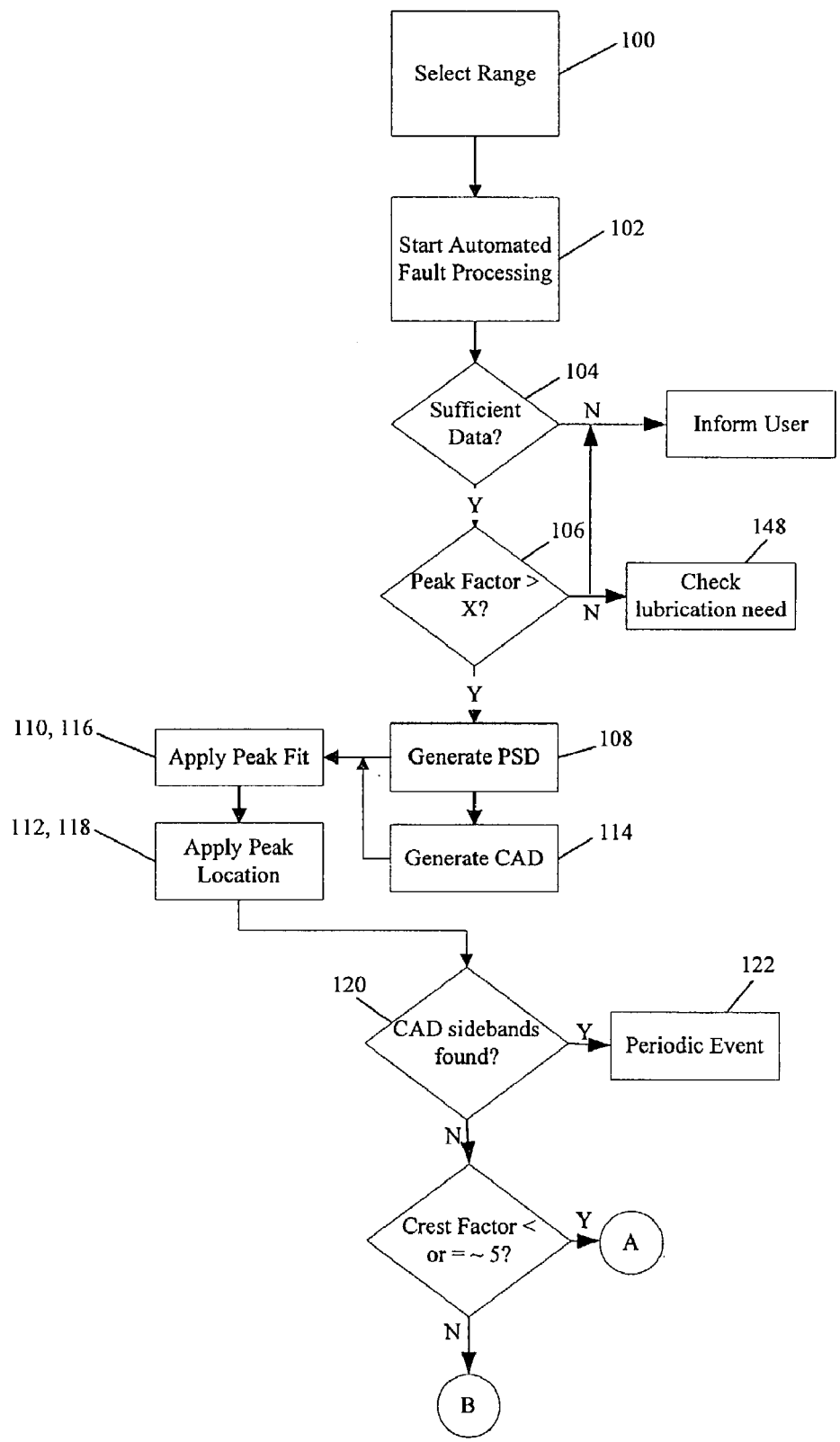
FIGS. 4A and 4B is a flowchart depicting a method of operating a diagnostic device to determine a periodic machine event.
Figure 4B:
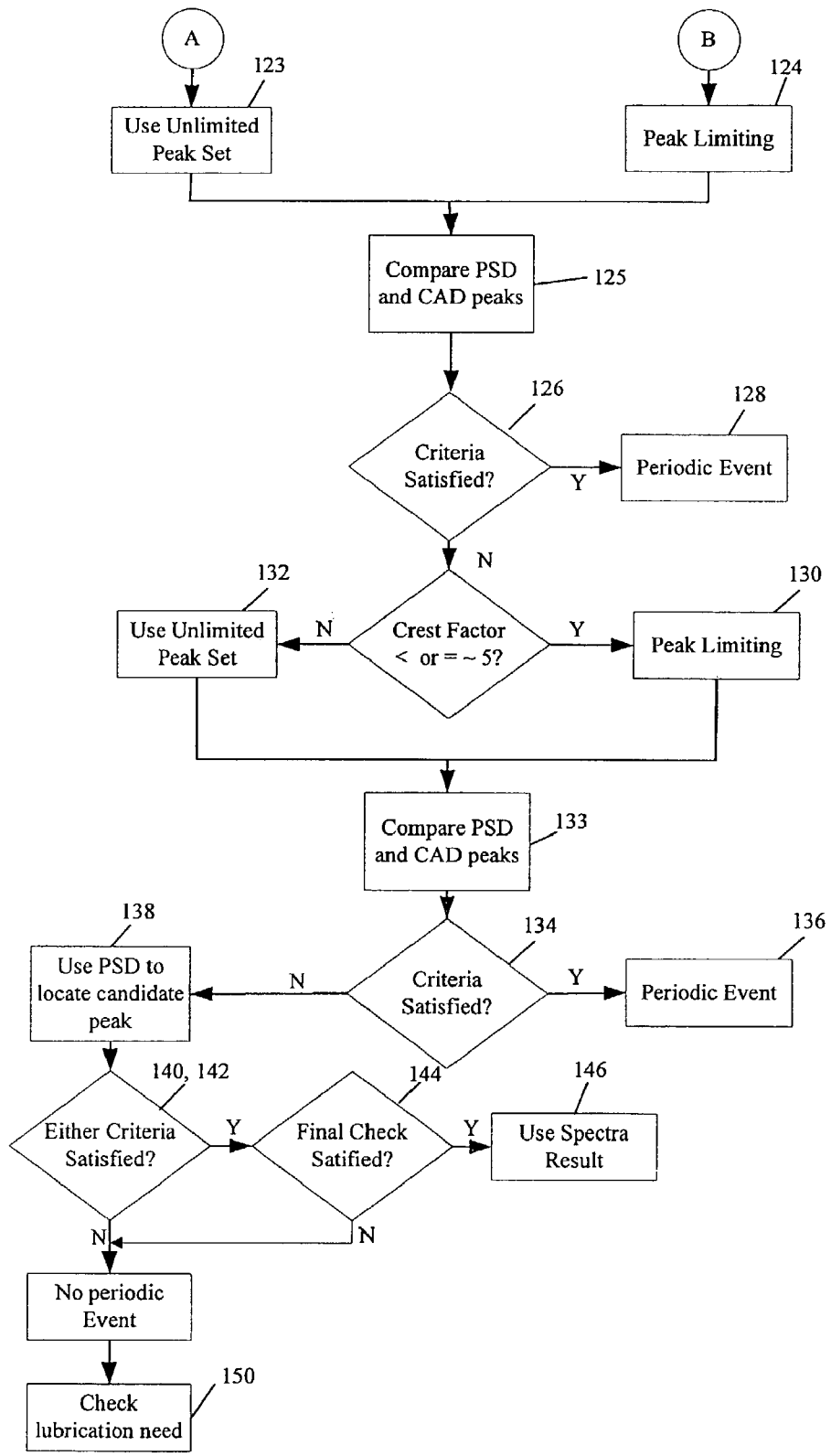

Referring now to FIGS. 4A and 4B, a preferred method of using the device 12 to determine an operational state or characteristic of a system 14 is depicted. It will be appreciated that the method can be included in firmware or software as instructions and/or sequences of instructions and the invention is not intended to be limited to any specific examples and/or embodiments described herein. The user 10 can use the keypads 64 to select a frequency range of interest to be used when processing and sensing signals emanating from the system 14 (step 100). For example, the user can select a revolution per minute (RPM) range from one of three ranges which can be a best estimate of the rotational speed of the machine under test. The selected range configures the device's signal processing components to operate within a specific range of frequencies. The range can be varied depending upon the particular diagnostic application and enables the device 12 to sense periodic signals/events emanating from the system 14.

Selecting a range also operates to set various parameters in the device 12. For example, some parameters include: the amount of waveform data collected and the number of lines in the resultant spectra; the waveform data sampling rate and hence the effective F-max (see below) for the resultant spectra; a minimum peak factor dB level below which the signal to noise ratio could be too low to verify periodic events; and, a minimum average dB level above which a determination for a machine's need for lubrication can be made.

After selecting a range of interest for the particular diagnostic application, the user 10 points and activates the device 12 by pulling the trigger. As described above, the sensor 22 is configured to receive signals emanating from the system 14. The device 12 informs the user 10 when sufficient waveform data has been collected. The user 10 then releases the trigger to begin automated fault diagnosis processing (step 102). A check is made to ensure that enough waveform data has been collected to perform the analysis (step 104). The user 10 is informed when the data collected is insufficient to perform the periodic event analysis. If enough data has been collected, then the peak factor of the collected data is checked to ensure that the peak factor of the data is large enough to perform an analysis (step 106). The user 10 is informed if the peak factor dB is too low to do a periodic event analysis.

The waveform data's mean value is subtracted out to thereby precondition the waveform data. Preferably, the device 12 uses the Fourier Transform function 66 on the preconditioned waveform data to generate frequency spectra or power spectral density (PSD) (step 108). Most preferably, the device 12 uses a hanning window while applying the Fourier Transform function 66 for the first time. The peak fit algorithm 70 and the peak locate algorithm 68 are then employed to find peaks in the PSD (steps 110 and 112). The peaks are preferably sorted from highest to lowest. The PSD is conditioned by setting the first two spectra bins to zero and setting the second half of the PSD to zero, thereby separating out the circular correlation function and producing a modified PSD.

The device 12 applies the Fourier Transform function 66 without a window to the modified PSD to produce raw autocorrelation data. The Fourier Transform function produces both real and imaginary data. Only the real portion of the raw autocorrelation data is stored and, preferably conditioned by changing negative and zero values to one, producing conditioned autocorrelation data (CAD) (step 114). This conditioned autocorrelation data is then stored in the second memory buffer 74. Next, peaks are located in the CAD by first applying the peak fit algorithm 70 and then applying the peak location algorithm 68 in the manner described previously (steps 116 and 118).

According to the preferred embodiment, PSD side bands around the 5 biggest peaks in the CAD are searched for candidate peaks (step 120). Preferably, the device 12 searches three different side bands wherein the side band frequencies are determined by the frequencies of the 3 highest peaks in the PSD. These side bands would also have to be at least about 20% of the fundamental peak's amplitude. Also, checks are made to make sure that there are no intervening peaks that are higher than a side band peak. If side bands are found on three of the five highest peaks in CAD, then the frequency of the PSD peak corresponding to that side-band frequency is a candidate for a periodic event of the machine under test. The device 12 displays that a periodic event has been found to the user 10 (step 122).

If no candidate frequency was found using the side band check described above, then the type of CAD graph is determined by a crest factor. The crest factor is defined as the highest amplitude in the CAD divided by the CAD's average amplitude. If the crest factor is less than about 5, the unlimited CAD peak set is first used for comparison with the PSD data, as described below (step 123). If the crest factor is greater than or equal to about 5, then peak limiting limits the CAD peak data (step 124) which is first used for the comparison with the PSD data (step 125).

Peak limiting, as described herein, is a process of limiting the CAD peaks based on certain criteria. Limiting of the CAD peaks is preferably based on spacing, iteratively limiting the CAD peaks looking at the largest peaks first. Most preferably, the process begins with the two largest peaks and attempts to add peaks into the set. For each peak added the following conditions must be met to see if the set is still valid:

A. Determine whether the smallest spacing between adjacent peaks in the set of peaks is greater than a number of bins (preferably about 5 bins). If it is not, then the maximum usable set of peaks has been found.

B. If the smallest spacing is greater than about 5, then check to ensure that all adjacent peaks in the set are integer multiples apart of the smallest distance. If not, then the maximum usable set of peaks has been found.

C. If the peaks are of the proper spacing, a check makes sure that there are peaks at all of the smallest distance multiples of the first peak. Peaks are added into the set if they are found. If there is a missing smallest distance multiple peak, then the maximum usable set of peaks has been found.

If any of the above failure conditions are met, the peak added to this set at the start of the current iteration is an invalid peak and is removed. Also, any other peaks added to the set on this iteration are removed. If the current set is valid, the next peak in the list is added for the next iteration. Once an invalid peak is found, it and all the remaining peaks are excluded from the AC peak list.

Next, the device 12 preferably checks to be sure that there is a true first peak in the set. The true first peak is the peak closest to zero that is of the smallest spacing between adjacent peaks in the limited set. If a true first peak can not be found, then there is no periodic activity. Lastly, a check is made to make sure there are at least 4 peaks in the set. If there are only three peaks in the set, an attempt is made to add a fourth peak at the proper smallest distance past the last peak.

Most preferably, the device 12 performs two comparisons when attempting to find a periodic event (step 125) using the limited or unlimited CAD peak data. First, the device 12 performs a search to find the closest autocorrelation (AC) peak corresponding to the highest PSD peak. If that fails, then a search is done to find the closest AC peak corresponding to the first PSD peak. In order for either of these searches to be successful, the following select criteria must be met (step 126). First, the searched for peak must preferably be a fundamental frequency peak and not a harmonic. Second, the peak must preferably be within about +/−2.5 bins of the exact frequency required. Third, there preferably needs to be about three harmonics of the fundamental peak. If all three of these cases are satisfied, then the resultant closest AC peak is a valid candidate for a periodic event of the machine under test (step 128).

If the device 12 does not locate a valid candidate at step 126 and the crest factor is less than about 5, then limited CAD peak data is used in the comparison with the PSD data (steps 130 and 133). If the device 12 does not locate a valid candidate at step 126 and the crest factor is greater than or equal to about 5, the unlimited CAD peak data is used in the comparison with the PSD data (steps 132 and 133). If the criteria is satisfied based on the result of the comparison at step 133, then the resultant closest AC peak is a valid candidate for a periodic event of the machine under test (steps 134 and 136).

If a candidate peak has not been located, then the device 12 uses the PSD to try to find a candidate peak (step 138). First, the device 12 searches for a peak at about ½ the frequency of the largest peak. A candidate peak must be within about 2% of the exact required location to be valid. If one is found, then a second search is done to find a peak at about 1.5 the frequency of the largest peak, again within about 2% of the exact required position. If both of these peaks are found, then the peak about ½ the frequency of the largest peak is a candidate peak based on spectral checking (step 140).

If one of those peaks is not found, then a peak is searched for at about 2 times the frequency of the largest peak, within about 2% of the exact required frequency. If this peak is found then the largest peak is a candidate peak based on spectral checking (step 142). If either of the sets of checks mentioned above passes, then a final spectral verification check is done on the candidate peak (step 144). This final check attempts to verify the result found in the spectra by seeing if corresponding 2×, 3× and 4× peaks exist in the CAD. If any two of these three peaks exist, then the spectra result can be used (step 146).

Finally, if the resultant candidate peak in the CAD has a corresponding peak in the PSD, the PSD peak is used as the frequency of the periodic event in the machine under test. Otherwise, the frequency of the peak in the CAD is converted and used as the frequency of the periodic event in the machine under test. The frequency of the periodic event is then reported to the user 10.

If the peak factor dB was too low to do a periodic event analysis or no periodic event was found on the machine under test, then a check is made to see if the machine needs to be lubricated (steps 148, 150). The average dB level of the machine is compared to the minimum average dB level that indicates a machine in need of lubrication. If the average dB level of the machine is higher, then the user 10 is informed that the machine needs lubrication. Lastly, if no other condition message was displayed, the user 10 is informed that the machine under test is OK.

According to an alternative embodiment, the device 12 uses the Fourier Transform function 66 on the preconditioned waveform data to generate frequency spectra or PSD.

Again, the device uses a hanning window while applying the Fourier Transform function 66 for the first time. During this time, the device 12 also maintains the digitized data or time waveform data in memory locations contained in the device 12. The device 12 performs successive, and preferably two Fourier Transform operations using the Fourier Transform function 66 on the digitized signals, thereby providing autocorrelation data or an "autocorelogram." It will be is appreciated that the term "autocorrelation data" is not intended to limit the invention to any specific autocorrelation theories, etc. As described below, the device 12 uses the autocorrelation data to provide diagnostic information including operational characteristics of the system 12 to the user 10.

According to the alternative embodiment, the autocorrelation data is used in conjunction with a set of algorithmic criteria stored in the firmware 62, to automatically determine an operational characteristic of the system 12 by detecting and outputting periodic events. Periodic signals emanating from the system 12 tend to appear highest in amplitude in the autocorrelation data or on a displayed autocorrelogram. The periodic signal or signals are usually harmonic in nature and are revealed in the autocorrelation data as peaks in multiples of the fundamental frequency.

Signals having little or no periodicity will not appear in the autocorrelation data. Random noise that might be included in the input signal sample, are generally not periodic in nature. Thus, these nonperiodic signals will not appear in the autocorrelation data. The autocorrelation function tends to "unmask" the desired periodic signals that are often not visible or recognizable in a simple time domain waveform (audibly or visually).

The device 12 packs and stores the data into memory buffers after generating the frequency spectrum data from the first application of the Fourier Transform function 66. The device 12 preferably includes two 16K memory buffers 72 and 74, as shown in the block diagram of FIG. 2. The first memory buffer 72 contains the frequency spectrum data output by the first application of the Fourier Transform function 66 to the digitized data. At this point, the second memory buffer 74 is preferably filled in with zeros or reset. Before transferring the frequency spectrum from the first memory buffer 72 to the second memory buffer 74, each data point in the first memory buffer 72 is preferably squared, and then converted to an integer in the range of about zero to about 32767. The integer data is then transferred to the second memory buffer 74.

In order to remove any DC offset, the first two data points in the second memory buffer 74 are set to zero. Zeros also fill in any excess data points in the second memory buffer 74. The device 12 preferably applies, a second Fourier Transform to the spectrum data in the second memory buffer 74 again using the Fourier Transform function 66, providing autocorrelation data. Most preferably, the device 12 applies a uniform window when applying the second Fourier Transform function 66 to obtain the autocorrelation data.

The second application of the Fourier Transform function 66 provides real and imaginary data. The real portion is stored into the second memory buffer 74. Negative values are set to zero and the positive values are squared before being stored. The peak location algorithm 68 examines the autocorrelation data stored in the second memory buffer 74 to determine a number of largest amplitude peaks, the twenty largest amplitude peaks, for example. Normally, the first few lowest frequency peaks have the highest amplitude, and the device 12 uses the peak location algorithm 68 to determine an operational state of the system 14 when a first (lowest frequency) peak satisfies the following criteria. The device 12 searches for the first (lowest frequency) peak within a group of peaks (the aforementioned number of largest peaks), and identifies the first peak as a candidate peak, and checks to see if it satisfies the following criteria:

A. The candidate peak is not located in one of a first set of frequency bins (most preferably the first ten lowest frequency bins), B. The candidate peak amplitude is greater than a number (most preferably about 0.30) multiplied by the largest amplitude in a select bin (most preferably the entire set of autocorrelation data), and C. There is another peak located at a frequency which is a multiple of the candidate peak frequency (most preferably about two times the candidate peak frequency (+or −Delta-F)) and also satisfies the criteria in A and B. If a candidate peak satisfies the criteria, it is marked as a qualified candidate peak, and a candidate peak fails to satisfy the criteria is marked as an unqualified candidate peak. After finding an unqualified candidate peak, the search moves to the next lowest frequency peak in the group and repeats the process of checking to see if the criteria is satisfied by the next candidate peak. The process in one embodiment continues only until one candidate peak is marked as qualified.

As used herein, Delta-F=(Fmax/number of lines of resolution). (Delta-T=1/(Fmax multiplied by 2.56)). However, it is appreciated that specific values and criteria may be changed according to the particular application. The device 12, according to the speed range selected by the user, automatically determines Fmax and the number of lines of resolution. The resolution is defined as the spacing between each data point.

In a different embodiment, once a candidate peak satisfies the required criteria, the device 12 checks for other peaks that the search routine might have missed. In the case of a repeating pattern, the signals emanating from the system 14 may have a plurality of periodic singularities which include substantial amplitudes. This can add many more peaks to the autocorrelation plot. The additional peaks can vary in amplitude, and the first few peaks may not always have the largest amplitudes.

As described above, the device 12 only selects a number of largest peaks in the data located in memory buffer 74. The peak location algorithm 68 may not select the correct peak if the first few lowest frequency peaks are not included in the peak list. To account for such an anomaly, the device 12 preferably stores a first number of lowest frequency peaks, the first 10 peaks for example, regardless of amplitude when the device 12 performs the peak search to store a predetermined number of the largest peaks. The peak location algorithm 68 proceeds as previously described and selects a peak from the list. According to this most preferred method, the device 12 searches the first number of lowest frequency peaks to determine if a candidate peak satisfies the criteria stored in firmware 62:

A. The peak amplitude is greater than about 0.90 multiplied by the amplitude of the originally chosen candidate peak, and B. Another peak is located at about two times the new candidate peak frequency (+or −Delta-F) that also satisfies the criteria in A.

If a candidate peak matches the above criteria, then the candidate peak is selected as an indicator of an operational state (related to a periodic event) of the system 14. When a numbers of peaks satisfy the above criteria, the selected peak will be the first peak (lowest frequency peak) from a group of harmonic peaks that occur in multiples of the fundamental frequency. Most preferably, the peak corresponding to the periodic event(s) is displayed on the display 56 to indicate a state of the machine.

In another alternate embodiment, a user selects an rpm range (rotational speed range) from one of three ranges. The user selects a rotational speed that is his best estimate of the rotational speed of the machine under test, and the selected range is provided to the device 12 through the keypads 64. A block of vibration data is received by the device 12 and is filtered to include only the selected range of frequencies corresponding to the selected rotational speed range indicated by the user. The data is stored in a first memory location within the memory 58.

Preferably several sets of data are taken within the selected rotational speed range, and Fourier transforms are performed on each set of data. The Fourier transforms produce spectrum data for each set of sampled data, and the multiple sets of spectrum data are averaged to produce a final set of spectrum data. Preferably, the spectrum data is stored in a first memory buffer 72, and the spectrum data is searched for a selected number of highest peaks, preferably the five highest peaks. The search is begun by first fitting a curve to the final set of spectrum data using the peak fit algorithm 70. Then, the peaks within the spectrum data are located using the peak location algorithm 68 and the selected number of highest peaks, such as five highest peaks, in the spectrum data are identified. Within the set of the five highest peaks, the lowest frequency peak (the first peak) is compared to the remaining four higher frequency peaks. If a predetermined number of the remaining four high-frequency peaks have a frequency that is an integer multiple of the first peak, then the first peak is identified as a candidate peak. Preferably the "predetermined number" is three, but, it may also be 1, 2 or 4. To constitute an integer multiple of the frequency of the lowest frequency peak, the higher frequency peak must have a frequency that is within 5% of a multiple of the lowest frequency. For example, if the lowest frequency is 1000 rpm, an integer multiple of that frequency would be 2000 rpm plus or minus 5%, 3000 rpm plus or minus 5%, etc.

Preferably additional conditioning is performed on the final set of spectrum data and a second Fourier transform function is performed on the conditioned spectrum data. The additional conditioning is performed to facilitate rapid calculation of the data during the next transform. The additional conditioning is performed by squaring each value in the spectrum data and then converting it (scaling the data) to an integer in the range of about zero to about 32,767. The conditioning further includes the process of removing D.C. offset by reducing the smallest data point to zero and reducing the remaining the values in the conditioned spectrum data by the same amount. Finally, zeros are preferably placed in any excess data points in the conditioned spectrum data.

The Fourier transform function 66 is then applied to the conditioned spectrum data to produce raw autocorrelation data. The Fourier transform produces both real and imaginary data. Only the real portion of the raw autocorrelation data is stored and, preferably, the real portion of the data is conditioned by changing negative values to 0 and the positive values are squared. This conditioned autocorrelation data is then stored in the second memory buffer 74. Next, peaks are located in the conditioned autocorrelation data by first applying the peak fit algorithm 70 and then applying the peak location algorithm 68 in the manner described previously. Preferably, the five highest peaks in the conditioned autocorrelation data are first identified, and then compared to the candidate peak frequency found in the spectrum data. If one of the autocorrelation peaks has a frequency that is equal to the candidate peak from the spectrum data, plus or minus 5%, then the candidate peak is qualified subject to final checks that are applied as discussed below. However, if the frequency of the candidate peak does not match of the frequency of any of the highest five autocorrelation peaks, plus or minus 5%, then the conditioned autocorrelation data is searched again to find a peak within the five highest peaks having a frequency that is an integer multiple of the frequency of the candidate peak, plus or minus 5%. If no peaks are found in the autocorrelation data that constitutes an integer multiple of the frequency of the candidate peak, then all five of the highest peaks in the conditioned autocorrelation data are compared to the five highest peaks in the spectrum data. If a matching peak is found, then it is determined to be a candidate peak that is qualified for the final checks referenced below. If no candidate peaks in the spectrum data are qualified in a manner discussed previously, a "no periodic events" message is displayed to user.

Once a candidate peak has met the criteria set forth above and is therefore qualified, two final checks are performed. The candidate peak must have a first harmonic. That is, the candidate peak in the spectrum data must have a first harmonic peak in the spectrum data having a frequency of two times the frequency of the candidate peak within plus or minus 5%. To meet this check, it is not necessary that the "first harmonic peak" of the candidate peak be within the five highest peaks in the spectrum data. For example, if the first harmonic peak was the seventh highest peak in the spectrum data, the candidate peak would still have a first harmonic peak and therefore would meet this first check. Secondly, the amplitude of the candidate peak must be more than 0.2 times the amplitude of the highest peak in the autocorrelation data. If the candidate peak satisfies all of the criteria set forth above, a "periodic events detected" message is displayed to the user. However, if the candidate peak fails to pass the final checks, or fails to meet any of the previously described criteria, a "no periodic events" message is displayed to the user.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A method of diagnosing a fault in a machine by determining a periodic event related to the fault in the machine, the method comprising:
   (a) sensing vibration signals emanating from the machine,
   (b) transforming the vibration signals to produce first transformed signals,
   (c) transforming the first transformed signals to produce second transformed signals having at least real components, and (d) processing the first and second transformed signals using select criteria to determine the periodic event.

2. The method of claim 1 wherein:
step (b) further comprises using a Fourier Transform function to transform vibration signals to produce the first transformed signals which comprise power spectral density data, and
step (c) further comprises using a Fourier Transform function to transform the first transformed signals to produce the second transformed signals which comprise autocorrelation data.

3. The method of claim 2 wherein step (d) further comprises locating one or more peaks in at least one of the power spectral density data and the autocorrelation data.

4. The method of claim 3 wherein step (d) further comprises performing peak comparisons using at least one peak in at least one of the power spectral density data and the autocorrelation data to determine a periodic event.

5. The method of claim 4 wherein step (d) further comprises applying select criteria to the comparisons to determine (1) whether a peak in the autocorrelation data is a fundamental frequency peak, (2) whether the peak in the autocorrelation data is within a number of bins of an exact frequency required, and (3) whether there are a select number of harmonics of the fundamental frequency peak.

6. The method of claim 3 wherein step (d) further comprises:
(d1) searching side bands of one or more peaks in the autocorrelation data based on a select peak frequency in the power spectral density data, and
(d2) determining a periodic event based at least in part on the searched side bands.

7. The method of claim 3 wherein step (d) further comprises:
(d1) limiting a number of peaks in the autocorrelation data,
(d2) comparing at least one peak in the limited autocorrelation data with at least one peak in the power spectral density data, and
(d3) determining the periodic event based at least in part on a result of the comparison.

8. The method of claim 3 wherein step (d) further comprises:
(d1) searching for a peak in the power spectral density data which represents a periodic event and
(d2) verifying that the peak represents a periodic event based at least in part on the autocorrelation data.

9. The method of claim 1 wherein step (d) further comprises:
(d1) examining the real components of the second transformed signals with a peak location algorithm, and
(d2) selecting a number of the real components of the second transformed signals when:
(1) a peak is not located in at least one of a first set of frequency bins;
(2) a first peak at a first peak frequency has an amplitude greater than a number multiplied by a largest amplitude peak in a selected bin; and
(3) a second peak is located at a second peak frequency which is related to the first peak frequency.

10. The method of claim 1 wherein step (d) further comprises:
(d1) storing peak magnitude data of the first transformed signals in a number of frequency bins,
(d2) determining a number of largest magnitude peaks from the stored peak magnitude data with a peak location algorithm,
(d3) locating a first peak within the number of largest magnitude peaks which corresponds to a periodic event of the system, and
(d4) determining whether the first peak satisfies select criteria.

11. The method of claim 10 wherein step (d) further comprises:
(d5) determining whether the first peak at a first frequency is located in a first frequency bin of a first set of frequency bins,
(d6) determining whether an amplitude of the first peak is greater than a number multiplied by a largest amplitude peak located in a second frequency bin of the first set of frequency bins,
(d7) determining whether a second peak is located at a second frequency which is about two times the first frequency of the first peak and which second frequency is located in a second set of frequency bins, and whether an amplitude of the second peak is greater than a number multiplied by the largest amplitude peak located in the second frequency bin, and
(d8) determining the periodic event based at least part on the first peak.

12. The method of claim 11 wherein step (d) further comprises:
(d9) determining whether a third peak at a third frequency has an amplitude greater than about 0.90 multiplied by the amplitude of the first peak,
(d10) determining whether a fourth peak at a fourth frequency which is about two times the third frequency has an amplitude greater than about 0.90 multiplied by the amplitude of the first peak, and
(d11) determining the periodic event based at least in part on the third peak.

13. A device for diagnosing a fault in a machine by determining a periodic event of the machine, the device comprising:
a sensor for sensing a vibration signal emanating from the machine, the sensor operable to convert the sensed vibration signal into an electrical signal,
signal processing components for digitizing the electrical signal to produce a digitized signal and for processing the digitized signal, and
firmware including at least one transform algorithm for successively transforming the digitized signal to produce first and second sets of transform data, where the second set of transform data is a transform of the first set of transform data, and at least one analysis algorithm for analyzing the first and second sets of transform data to determine the periodic event based on select criteria applied to the first and second sets of transform data.

14. The device of claim 13 wherein the at least one transform algorithm further comprises a Fourier Transform algorithm for transforming the digitized signal to produce power spectral density data.

15. The device of claim 14 wherein the firmware further comprises algorithmic structure for applying the Fourier Transform algorithm to the power spectral density data to produce autocorrelation data and for conditioning the autocorrelation data to produce conditioned autocorrelation data.

16. The device of claim 15 wherein the at least one analysis algorithm further comprises a peak fit algorithm for fitting a curve to the power spectral data and the conditioned autocorrelation data, and a peak location algorithm for locating one or more peaks in the power spectral data and the conditioned autocorrelation data.

17. The device of claim 16 wherein the at least one analysis algorithm further comprises a sideband search algorithm for searching side bands of one or more peaks in the conditioned auto correlation data based at least in part on a select peak frequency of the power spectral density data, and for determining a periodic event based at least in part on the searched side bands.

18. The device of claim 16 wherein the at least one analysis algorithm further comprises a peak comparison algorithm for comparing at least one peak in the conditioned autocorrelation data with at least one peak in the power spectral density data, wherein search criteria applied to a result of the peak comparison determines whether a periodic event exists.

19. The device of claim 18 wherein the search criteria further comprises instructions for determining whether the at least one peak in the conditioned autocorrelation data is a fundamental frequency peak, whether the at least one peak in the conditioned autocorrelation data is within a number of bins of an exact frequency required, and whether there are a select number of harmonics of the fundamental frequency peak.

20. The device of claim 16 wherein the at least one analysis algorithm further comprises a peak comparison algorithm for limiting a number of peaks in the conditioned autocorrelation data and for comparing at least one peak in the limited autocorrelation data with at least one peak in the power spectral density data, wherein a result of the comparison is used to determine whether a periodic event exists.

21. The device of claim 16 wherein the at least one analysis algorithm further comprises a peak search algorithm for searching for a peak in the power spectral density data which represents a periodic event and for verifying that the peak in the power spectral density data corresponds to a periodic event based at least in part on the conditioned autocorrelation data.

22. An apparatus for diagnosing a fault in a machine, the apparatus comprising:
   a sensor for sensing a vibration signal emanating from the machine,
   analog to digital processing components for digitizing the sensed vibration signal to produce a digitized signal,
   at least one transform algorithm for transforming the digitized signal to generate power spectral density data and autocorrelation data from the digitized signal,
   memory for storing the power spectral density data and auto correlation data,
   at least one analysis algorithm for analyzing the power spectral density and autocorrelation data, the analysis algorithm including criteria for determining a periodic event of the machine based at least in part on the autocorrelation data, and a display for displaying the periodic event to a user.

23. The apparatus of claim 22 wherein the at least one transform algorithm further comprises a Fourier Transform function for producing the power spectral density data when the Fourier Transform function is first applied to the digitized signal and for producing autocorrelation data when the Fourier Transform function is thereafter applied tote power spectral density data, and wherein the apparatus determines the periodic event based at least in part on one or more peaks in at least one of the power spectral density data and the autocorrelation data.

* * * * *